United States Patent
Kosheleva et al.

(10) Patent No.: US 9,138,476 B2
(45) Date of Patent: Sep. 22, 2015

(54) NANOPARTICLE-ASSISTED ULTRASOUND FOR CANCER THERAPY

(71) Applicant: Academia Sinica, Taipei (TW)

(72) Inventors: Olga K. Kosheleva, Taipei (TW); Peter Lai, New Taipei (TW); Nelson G. Chen, Knoxvile, TN (US); Michael Hsiao, New Taipei (TW); Chung-Hsuan Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/253,977

(22) Filed: Apr. 16, 2014

(65) Prior Publication Data

US 2014/0335156 A1    Nov. 13, 2014

Related U.S. Application Data (60) Provisional application No. 61/812,348, filed on Apr. 16, 2013.

(51) Int. Cl.
  *A61N 7/00* (2006.01)
  *A61K 41/00* (2006.01)

(52) U.S. Cl.
  CPC .............. *A61K 41/0033* (2013.01); *A61N 7/00* (2013.01); *Y10S 977/911* (2013.01)

(58) Field of Classification Search
  CPC ............... A61L 7/00; A61L 7/02; A61L 7/04
  See application file for complete search history.

(56) References Cited

U.S. PATENT DOCUMENTS

| | | | |
|---|---|---|---|
| 2003/0003055 A1* | 1/2003 | Unger et al. ................. | 424/9.51 |
| 2007/0098713 A1* | 5/2007 | Unger et al. ................. | 424/133.1 |
| 2008/0045865 A1* | 2/2008 | Kislev ............................... | 601/3 |
| 2010/0266508 A1* | 10/2010 | Kattumuri et al. ........... | 424/9.42 |

OTHER PUBLICATIONS

ST Kang, YL Luo, YF HUang, CK Yeh. "DNA-Conjugated Gold Nanoparticles for Ultrasound Targeted Drug Delivery." 2012 IEEE International Ultrasonics Symposium Proceedings, pp. 1866-1868.*
IEEE Explore Digital Library. http://ieeexplore.ieee.org/xpls/abs_all.jsp?arnumber=6562489, accessed Aug. 15, 2014, 2 printed pages.*
N Tang, G Du, N Wang, C Liu, H Hang, W Liang. "Improving Penetration in Tumors With Nanoassemblies of Phospholipids and Doxorubicin." Journal of the National Cancer Institute, vol. 99, 2007, pp. 1004-1015.*

* cited by examiner

*Primary Examiner* — Isaac Shomer
(74) *Attorney, Agent, or Firm* — Eckman Basu LLP (57) ABSTRACT

Methods for killing cancer cells and treating cancer in a subject by exposing the cells to nanoparticles, and irradiating with a focused, low to medium power ultrasound. The nanoparticles can be gold, iron oxide, copper, silver, polystyrene, PEG, or liposome nanoparticles. The nanoparticles can have a cancer drug attached, such as an antibody-based cancer drug.

8 Claims, 5 Drawing Sheets
(2 of 5 Drawing Sheet(s) Filed in Color)

NANOPARTICLE-ASSISTED ULTRASOUND FOR CANCER THERAPY

BACKGROUND OF THE INVENTION

Cancer is one of the top two causes of death throughout the world. Many cancer patients die from the serious side effects of chemotherapy or from a relapse after the treatment. The serious side effects are largely due to the destruction of normal cells. The immune system and normal organ functions can be compromised by these treatments.

Cancer therapies have often been based on drugs or surgery or both. For many cancers, surgical treatments may be unsuccessful. Chemotherapy has major drawbacks in that it causes damage to healthy cells and it leads to drug-resistant cancer cells becoming the dominant species. Radiation therapy often has serious side effects because radiation must pass through overlaying tissues. Photon therapy is largely limited to tumors near the skin surfaces.

The chemical approach is based on drugs that are toxic to malignant tumor cells. Unfortunately, most cancer drugs, especially chemotherapy drugs, are also harmful to normal cells and can distinguish little between cancer cells and normal cells. Both "passive" tumor targeting, which utilizes tumor-selective enhanced permeability, and "active" tumor targeting, which is based on the specific interactions between drugs and cancer cell markers, have been used to reduce side effects. Nevertheless, the side effects have not been eliminated, and the targeting drugs are typically costly. Most cancers are highly heterogeneous; an estimated number of more than 100 different types of cells can co-exist in one tumor. When a specific drug is used, some specific cancer cells with resistance to that drug may survive while other cancer cells are killed. These drug-resistant cells then replicate and become the dominant type of cells in the tumor, rendering the drug useless in treating that tumor. Thus, chemotherapy can have a high failure rate due to drug resistance.

Radiation therapy is a physical method of cancer treatment that may utilize ionizing radiation from electromagnetic waves, such as gamma rays or x-rays, particles such as electrons, protons, neutrons and alpha particles, and non-ionizing radiation such as light, microwaves, and radio waves. These forms of radiation have different energy levels and can penetrate cells to varying extents. The ionizing radiation is intended to be directed only at the tumor. However, because the radiation is difficult to focus, it can also affect the normal tissues as it passes through the patient's body. Thus, normal cells are affected by ionizing radiation, which causes undesirable side effects. Ionizing radiation itself may cause DNA mutation in normal cells, causing them to become cancerous.

Light as non-ionizing radiation is used as a photodynamic therapy for tumors. Photodynamic therapy transforms oxygen into reactive oxygen species (ROS) inside the cells and subsequently induces cell apoptosis and necrosis. One of the major limitations of photodynamic methods is that solid tumor cells become oxygen deficient. Hypoxic cells are known to be resistant to photodynamic therapy. Other drawbacks of photodynamic therapy are limited ability to penetrate the body and the requirement of toxic dyes.

Other non-ionizing radiation therapies are largely based on the hyperthermia of tumors caused by radio waves and ultrasound. Clinical examinations indicate that malignant cells subjected to hyperthermia killing are more sensitive than their normal counterparts.

Ultrasound and radiofrequency waves may achieve non-intrusive therapy or imaging by penetrating deep inside the human body without harming the tissues. The disadvantage of the therapies based on radio-frequency electromagnetic waves is the need for high-power radiofrequency which can lead to serious side effects.

Unlike radiofrequency, ultrasound (US) can be easily focused onto a small, well-defined area of interest. Focused ultrasound is a non-intrusive technology that can be used to generate local hyperthermia. Focused ultrasound can be used for tumor ablation. However, while a high-intensity focused ultrasound (HIFU) can ablate tumors deep within the body without harming the overlying skin or adjacent connective tissues, normal cells near the tumor region are killed by the intense ultrasound.

There is a continuing need for methods to improve outcomes and reduce side effects in cancer treatment. There is also a need for compositions, formulations, materials and methods to improve outcomes and reduce side effects in treatment of cancers. More particularly, there is a need for methods that reduce the level of ionizing radiation in cancer treatment. There is also a need for methods that reduce the destruction of normal cells in cancer treatment. There is a further need for methods in cancer treatment that avoid drug-resistant cancer cells becoming dominant. There is also a need for methods in cancer treatment that avoid development of drug-resistant cancer cells.

BRIEF SUMMARY OF THE INVENTION

This invention relates to the fields of cancer treatment and cancer therapy. More particularly, this invention relates to a delivering a drug for cancer treatment and killing cancer cells by employing low to medium intensity ultrasound and nanoparticles to enhance absorption by the cancer cells. Cancer cells are destroyed and side effects are reduced.

This invention encompasses methods and materials for cancer treatments. In some aspects, ultrasound radiation is used to enhance the delivery or effect of nanoparticles on cancer cells. The compositions, formulations, materials and methods of this invention can be used for killing cancer cells in tissues, tumors, organs, or cells of a subject. The subject may be human or non-human.

In some embodiments, nanoparticles may be used to kill cancer cells. The cancer cells may be localized in tissues, or in tumors.

In certain embodiments, the absorption of nanoparticles by cells or tumors may be increased by applying ultrasound radiation. The ultrasonic radiation can be tightly focused onto a small target volume or tumor to reduce, minimize or eliminate damage to other tissues or organs that surround the target. By enhancing the absorption of nanoparticles, the cancer treatment benefits by killing a greater percentage of cancer cells than the surrounding cells.

Embodiments of this invention include:

A method for treating cancer in a subject, comprising the steps: administering nanoparticles to the subject; and irradiating the subject with a focused, low to medium power ultrasound.

A method for uptake of a drug for treating cancer in a subject, the method comprising the steps: administering to the subject nanoparticles having the drug attached; and irradiating the subject with a focused, low to medium power ultrasound.

The method above, wherein the nanoparticles are gold, iron oxide, copper, silver, polystyrene, PEG, or liposome nanoparticles. The method above, wherein the nanoparticles are magnetic or non-magnetic. The method above, wherein the nanoparticles are paramagnetic.

The method above, wherein the nanoparticles have a cancer drug attached. The method above, wherein the cancer drug is a targeted cancer drug, a humanized monoclonal antibody drug, a chimeric monoclonal antibody drug, or a fully human antibody drug.

The method above, wherein the size of the nanoparticles ranges from 1 nanometer to 1000 nanometers, or from 2 to 500 nm, or from 2 to 200 nm, or from 2 to 100 nm, or from 10 to 500 nm, or from 10 to 300 nm, or from 10 to 200 nm, or from 10 to 150 nm, or from 10 to 100 nm, or from 10 to 60 nm.

The method above, wherein the size of the nanoparticles is 1 nanometer, or 2 nm, or 3 nm, or 4 nm, or 5 nm, or 6 nm, or 7 nm, or 8 nm, or 9 nm, or 10 nm, or 20 nm, or 30 nm, or 40 nm, or 50 nm, or 60 nm, or 70 nm, or 80 nm, or 90 nm, or 100 nm, or 120 nm, or 140 nm, or 160 nm, or 180 nm, or 200 nm, or 220 nm, or 240 nm, or 260 nm, or 280 nm, or 300 nm.

The method above, wherein the power of the ultrasound is less than or equal to that used in HIFU. The method above, wherein the intensity power of the ultrasound is less than 30 Watts/cm$^2$. The method above, wherein the power of the ultrasound is less than 20 Watts/cm$^2$. The method above, wherein the power of the ultrasound is less than 10 Watts/cm$^2$. The method above, wherein the power of the ultrasound is less than 8 Watts/cm$^2$. The method above, wherein the power of the ultrasound is less than 3 Watts/cm$^2$.

The method above, wherein the ISPTP intensity of the ultrasound is less than 200 W/cm$^2$. The method above, wherein the ISPTP intensity of the ultrasound is less than 150 W/cm$^2$. The method above, wherein the ISPTP intensity of the ultrasound is less than 100 W/cm$^2$. The method above, wherein the ISPTP intensity of the ultrasound is less than 70 W/cm$^2$. The method above, wherein the ISPTP intensity of the ultrasound is less than 30 W/cm$^2$. The method above, wherein the ISPTP intensity of the ultrasound is less than 20 W/cm$^2$. The method above, wherein the ISPTP intensity of the ultrasound is less than 10 W/cm$^2$. The method above, wherein the ISPTP intensity of the ultrasound is less than 8 W/cm$^2$. The method above, wherein the ISPTP intensity of the ultrasound is less than 3 W/cm$^2$. The method above, wherein the subject is human or non-human.

The method above, wherein the administration is by parenteral injection, intravenous injection, intra-arterial injection, intramuscular injection, subcutaneous injection, oral, dietary, inhalation, aerosol, or nasal.

The method above, wherein the nanoparticles are administered in solution, emulsion, gels, aerosols, or capsules.

The method above, wherein the gold nanoparticles are administered at a concentration of injected gold of 50 mg Au/cm$^3$, or 75 mg Au/cm$^3$, or 100 mg Au/cm$^3$, or 150 mg Au/cm$^3$, or 200 mg Au/cm$^3$, or 250 mg Au/cm$^3$.

The method above, wherein the nanoparticles are administered at a volume injected of 0.001 ml/g of subject weight, or 0.002 ml/g of subject weight, or 0.003 ml/g of subject weight, or 0.005 ml/g of subject weight, or 0.008 ml/g of subject weight, or 0.01 ml/g of subject weight, or 0.02 ml/g of subject weight, or 0.03 ml/g of subject weight, or 0.04 ml/g of subject weight, or 0.05 ml/g of subject weight.

A method for killing cancer cells, comprising the steps: exposing the cells to nanoparticles; and irradiating the cells with a focused, low to medium power ultrasound.

A method for killing cancer cells with reduced ionizing radiation, comprising the steps: exposing the cells to nanoparticles; and irradiating the cells with a focused, low to medium power ultrasound.

A method for killing cancer cells with reduced development of drug-resistant cancer cells, comprising the steps: exposing the cells to nanoparticles; and irradiating the cells with a focused, low to medium power ultrasound.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, or limited to any preferred embodiments, and the scope of the present invention is defined by the appended claims.

BRIEF DESCRIPTION OF THE DRAWINGS

This patent or application file contains at least one drawing executed in color. Copies of this patent or patent application publication with color drawings will be provided by the US Patent Office upon request and payment of the necessary fee.

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Embodiments of this invention provide methods for cancer treatment and cancer therapy. In some aspects, this invention provides cancer treatments employing focused, low to medium intensity ultrasound and nanoparticles to enhance absorption by the cancer cells.

This invention can provide distinctions in cell death between normal and cancer cells when they are exposed to the combination of focused ultrasound with nanoparticles. These distinctions can help to reduce the side effects of tumor treatment and provide a novel treatment modality.

The non-intrusive methods of this disclosure can provide a high degree of temporal and spatial control of the treatment of cancers, as well as continuous monitoring by ultrasonic imaging.

In some embodiments, nanoparticle-assisted ultrasound therapy (NAUT) can provide an effective new tool for cancer treatment. In nanoparticle-assisted ultrasound therapy, cancer cells may be killed while the development of drug-resistant cancer cells is reduced. Ultrasound may be used advantageously to penetrate deep into the body without limit for cancer treatment, and may not require dye labeling.

In some aspects, ultrasound radiation is utilized at low power intensity. With low power intensity ultrasound side effects may be reduced or eliminated.

In some embodiments, the power of the ultrasound used is less than 30 Watts/cm$^2$. In some embodiments, the power of the ultrasound used is less than 20 Watts/cm$^2$. In some embodiments, the power of the ultrasound used is less than 15 Watts/cm$^2$. In some embodiments, the power of the ultrasound used is less than 10 Watts/cm$^2$. In some embodiments, the power of the ultrasound used is less than 8 Watts/cm$^2$. In some embodiments, the power of the ultrasound used is less than 3 Watts/cm$^2$.

In some embodiments, cancer cells may be destroyed while side effects can be reduced.

Embodiments of this invention may employ non-toxic gold and/or magnetic nanoparticles for cancer treatment.

In some embodiments, the nanoparticles can be gold, iron oxide, copper, silver, polystyrene, PEG, or liposome nanoparticles.

In further embodiments, the nanoparticles have a cancer drug attached. In certain embodiments, the cancer drug is a targeted cancer drug, a humanized monoclonal antibody drug, a chimeric monoclonal antibody drug, or a fully human antibody drug.

The nanoparticles of this disclosure may have any shape, including spherical particles and rod shaped particles.

The size of nanoparticles of this disclosure may range from 1 nanometer to 1000 nanometers, or from 2 to 500 nm, or from 2 to 200 nm, or from 2 to 100 nm, or from 10 to 500 nm, or from 10 to 300 nm, or from 10 to 200 nm, or from 10 to 150 nm, or from 10 to 100 nm, or from 10 to 60 nm.

The size of nanoparticles of this disclosure may be 1 nanometer, or 2 nm, or 3 nm, or 4 nm, or 5 nm, or 6 nm, or 7 nm, or 8 nm, or 9 nm, or 10 nm, or 20 nm, or 30 nm, or 40 nm, or 50 nm, or 60 nm, or 70 nm, or 80 nm, or 90 nm, or 100 nm, or 120 nm, or 140 nm, or 160 nm, or 180 nm, or 200 nm, or 220 nm, or 240 nm, or 260 nm, or 280 nm, or 300 nm.

The compositions, formulations, materials and methods of this invention can be effective on all different kinds of tumors. In certain embodiments, the formulations and methods of this invention can be effective against cancers with high heterogeneity of cancer cells that would otherwise develop drug-resistance-related relapse. Treatments of this disclosure may not lead to an increase in the population of drug-resistant cancer cells.

In some aspects, the formulations and methods of this disclosure may selectively kill cancer cells with little or no effect on healthy, normal cells.

Embodiments of this invention encompass compositions and formulations including gold and/or magnetic nanoparticles (NP).

In one aspect, low to medium-intensity ultrasound can be used to treat tumor cells which are exposed to compositions and/or formulations containing gold and/or magnetic nanoparticles. The ultrasound radiation intensity can advantageously be reduced over that used in HIFU, allowing nearby normal cells to survive the treatment.

In some embodiments, a treatment of this disclosure provides cancer cell death enhanced by adding nanoparticles to the cell culture. Cancer cells may be preferentially destroyed over normal cells.

In further embodiments, methods for ultrasound treatment of this disclosure with nanoparticle formulations can be rendered more effective to kill cancer cells, or to do greater damage to cancer cells than normal cells, than treatment without nanoparticles.

In certain embodiments, methods for ultrasound treatment of this disclosure with nanoparticle formulations that reduce the intensity of ultrasound can be used for cancer growing near a critical region of an organ, for example, as for some brain cancers.

Embodiments of this disclosure include using medium-intensity ultrasound for the treatment of malignant and non-malignant cells. Cells may be subjected to formulations containing a low-concentration of gold nanoparticles. Using a non-toxic concentration of gold nanoparticles advantageously reduces toxicity due to the nanoparticles themselves. Malignant cells with a monolayer on the substrate can be rendered more sensitive to the effect of ultrasound than non-malignant cells. The use of formulations containing non-toxic gold nanoparticles can increase the death of malignant cells via ultrasound.

In some embodiments, ultrasound in combination with nanoparticles can kill malignant cells more effectively and selectively than normal cells.

Methods and formulations of this invention can reduce side effects found in tumor treatment using chemical drugs. In certain aspects, methods of this disclosure provide a higher selectivity toward cancer cells.

Methods of this invention can use precise focusing and control of the ultrasound energy. In some aspects, non-toxic and low-dose nanoparticles may be used. In further aspects, low power ultrasound is used.

In some embodiments, use of ultrasound in the presence of gold nanoparticles can promote the permeability of cells to increase the nanoparticle uptake. In certain embodiments, methods of this invention may activate pores in cell membranes.

In further embodiments, gold and/or super-paramagnetic iron oxide nanoparticles may act as radio-sensitizers.

Other metal nanoparticles such as Cu, Ag and non-metal nanoparticles such as PEG and polystyrenes can also be used.

In some embodiments, targeted drugs attached to nanoparticles can also be used.

In another aspect, gold nanoparticles can simultaneously be used to visualize their location inside the body using photoacoustic imaging or optical coherence tomography in combination with X-ray imaging or electron microscopy.

In certain embodiments, NAUT can be combined with conventional treatments to improve cancer treatment outcomes and increase cure rates.

In one aspect, superparamagnetic iron oxide nanoparticles can be used which are magnetic resonance imaging (MRI) contrast agents for magnetic hyperthermia of cancer.

In some embodiments, the nanoparticle formulation can be delivered by various routes of administration including parenteral, intravenous injection, intra-arterial injection, intramuscular injection, subcutaneous injection, oral, dietary, inhalation, aerosol, or nasal. Formulation of the nanoparticles can be in solution, emulsion, gels, aerosols, or capsules. A composition of the nanoparticles can be made in a physiologically acceptable vehicle or carrier. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

Some examples of materials and formulations are found in Joseph Price Remington, Remington's Pharmaceutical Sciences, 16th Edition, Mack, Ed. (1980); Joseph Price Remington, The Science and Practice of Pharmacy (2006).

In certain embodiments, gold nanoparticles may be administered at a concentration of injected gold of 50 mg Au/cm$^3$, or 75 mg Au/cm$^3$, or 100 mg Au/cm$^3$, or 150 mg Au/cm$^3$, or 200 mg Au/cm$^3$, or 250 mg Au/cm$^3$.

In certain embodiments, gold nanoparticles may be administered at a volume injected of 0.001 ml/g of subject weight, or 0.002 ml/g of subject weight, or 0.003 ml/g of subject weight, or 0.005 ml/g of subject weight, or 0.008 ml/g of subject weight, or 0.01 ml/g of subject weight, or 0.02 ml/g of subject weight, or 0.03 ml/g of subject weight, or 0.04 ml/g of subject weight, or 0.05 ml/g of subject weight.

Nanoparticles may be suspended in phosphate-buffered saline at pH 7.4.

Example 1

Summary

Low to medium-intensity ultrasound was used from an HIFU system for the comparative treatment of malignant (A549) and non-malignant (Beas-2B) lung epithelial cells. Low-concentration (2.5 ppm) gold nanoparticles were added into the cell lines, which were then subjected to ultrasound radiation.

It was found that malignant cells with a monolayer on the substrate were more sensitive to the effect of ultrasound than non-malignant cells. The addition of non-toxic gold nanoparticles further enhanced the death of malignant cells via ultrasound. The treatment of co-cultured A549 and Beas-2B monolayers also exhibited greater damage to malignant cells. Similar conclusions were found for malignant MDA-MB231 and non-malignant MCF-10A and H-184B5F5/M10 breast cells with gold and magnetic nanoparticles.

Example 2

Cell Cultures and Nanoparticle Treatment

Human A549, lung alveolar adenocarcinoma, and BEAS-2B, immortalized human bronchial epithelial cells, were obtained from ATCC (Manassas, Va., USA). The A549 cells were cultured in Dulbecco's modified Eagle's medium (DMEM) with 10% fetal bovine serum (FBS). Defined Keratinocyte-SFM culture media (KSFM; Gibco Cell Culture, USA) was used for the Beas-2B cells. The cells were cultured separately in a monolayer fashion with concentrations of 5×105 cells/well/mL or in a co-culture (1:1) with a total concentration of 4×105 cells/well/mL. To create a co-culture, monolayers of A549 and BEAS-2B cells were marked with red and green fluorescent proteins, respectively. The cells were mixed and incubated in DMEM with 10% FBS overnight in a 12-well polystyrene culture plate (Costar 3513, Corning, USA) at 37° C. in 5% CO2. Just prior to ultrasound treatment, the cells were washed twice with 1 mL PBS and 1 mL freshly prepared DMEM with 10% FBS. Then, a 50-μL gold nanoparticle suspension (BBI International Co., 10 nm, stock concentration=50 μg Au/mL) was added to the wells to achieve a concentration of 2.5 μg Au/mL. In other cases, magnetic nanoparticles were used for the test. 50 μL of aminodextran coated magnetic nanoparticles (MagQu Co., Taiwan, size 60 nm) was added to a well to a final concentration of 60 μg Fe/mL in cell suspension. One of two similar culture plates was used for the ultrasound treatment, while the other plate was used as the control.

Example 3

Ultrasound Setting and Treatment

The SONABLATE 500 (Focus Surgery Inc., USA) was chosen as the ultrasound source for cell irradiation. The dual-element self-focusing transducer used in therapy mode had a 4-MHz resonant frequency and a 4-cm focal length. The probe was placed in the water tank with 4.5 L degassed water for cell irradiation. The distilled water was obtained with a Millipore Q Synthesis A10 water purification system (resistivity=18 MOhm/cm, TOC=3 ppb) and was degassed for 3 hours using an in-line membrane vacuum degasser (ERC 3000 W/N, Endeavor Responsibility Challenge Co, Japan). The oxygen concentration in the water was measured prior to the experiments using an oxygen (dissolved) CHEMets Kit (K-7512, CHEMetrics Inc., USA) and was estimated at 2-3 ppm. The water was at a room temperature of 24-25° C. The ultrasound power was adjusted using the software in the SONABLATE 500. The shape of the ultrasound focal spot was a 3-mm-wide by 12-mm-high prolate spheroid. The transducer was operated in a scanning regime and irradiated 25 spots (5×5) in the 15×15-mm area under a well. Thus, the treated region was a 3D 15×15×12-mm rectangular figure and was centered under the well. However, the center of the focal spot (with the maximum ultrasound intensity) was fixed at a distance of 3 mm under the culture plate's surface. Each spot was irradiated for 3 seconds. The size and location of the treated zone were similar for each well in the culture plate. Every well was treated three times with ultrasound. The temperature of the culture media in a well was measured after 3 treatments using a thermocouple, and the temperature change was found to be less than 0.1° C. Thus, the thermal effect of ultrasound during treatment was negligible. The spatial-peak temporal-peak intensity (ISPTP) in a well with 1 mL water was measured via calibrated needle hydrophone (HNA-0400) with a pre-amplifier (AH-2020-0003, Onda, Calif., USA). For an ultrasound power setting of 8 W, the machine-attached software estimated an ISPTP of 69 W/cm$^2$ with corresponding negative pressure of 1 MPa. The range of the ultrasound power can be adjusted using the software to cover a range from 1 to 37 W. For typical prostate cancer surgery, the power was set at 37 W. With nanoparticle uptake by the cells, we found that the power required to kill malignant cells was significantly reduced to 8 W.

Example 4

Flow Cytometry Analysis

After the ultrasound treatment of the separate BEAS-2B and A549 cell cultures, all cells from each well were collected using trypsin in a final volume of 2 mL cell suspension and premixed with 1 ppm of propidium iodide (Sigma Aldrich, USA). Flow cytometry was performed with a BD FACS Canto II system (BD Biosciences, USA) using a 488-nm laser for excitation and a PE channel for fluorescence detection.

The live cells (Q4) were counted before and after the ultrasound exposure using BD FACS Diva Software 6.0.

Example 5

Microscopic Examinations and Quantitative Analysis

For the co-culture of BEAS-2B and A549 cells after ultrasound treatment, the floating cells were analyzed under an optical microscope (the number of floating cells was small and approximately the same for both cell lines) and subsequently discarded. The attached cells were washed with 1 mL PBS, followed by washing with an additional 1 mL PBS with 0.1 mL 0.4% trypan blue for 5 minutes. The phase contrast images of the attached cell monolayers were obtained via optical microscopy (Olympus IX71, USA) with 200× magnification and a digital camera (Olympus DP70). A mercury lamp (U-LH100$_{HG}$) was used to produce separate fluorescent images of the cells modified with the fluorescent proteins.

Example 6

Transmission Electron Microscopy (TEM)

Transmission electron microscopy of healthy breast H-184B5F5/M10 and cancerous MDA-MB-231 cells was performed using the following procedure: cells before and after ultrasound exposure were collected and fixed in 2.5% glutaraldehyde and 0.1 M cacodylate buffer for two hours at 4° C. The cells were washed twice in the cacodylate buffer for 15 minutes each. A secondary fixation was performed in 1% osmium tetroxide for one hour at 4° C., followed by two more 15-minute wash in the same buffer. After dehydration, the material was embedded in Spurr's resin. The resin was first diluted in acetone (1:1) and incubated at 4° C. with agitation for 2 hours, and then diluted in acetone (1:3) and incubated at 4° C. with agitation for 24 hours. The pellet was transferred to a pure Spurr's resin and incubated at 60° C. for 48 hours until completely polymerized. Sections of 70-90 nm were obtained using a Leica EM UC 7 ultramicrotome (Leica Microsystems GmbH). The sections were then placed on copper grids and were studied under a TEM (TEM Hitachi H-7000, High-Technologies Co., Japan).

Example 7

Gold Nanoparticles with Low Power Ultrasound

The effect of ultrasound on lung cancer A549 and "normal" BEAS-2B cells cultured separately as monolayers in a 12-well culture plate was analyzed by counting the living cells (Q4), which were defined by propidium iodide staining and flow cytometry.

Figure 1:
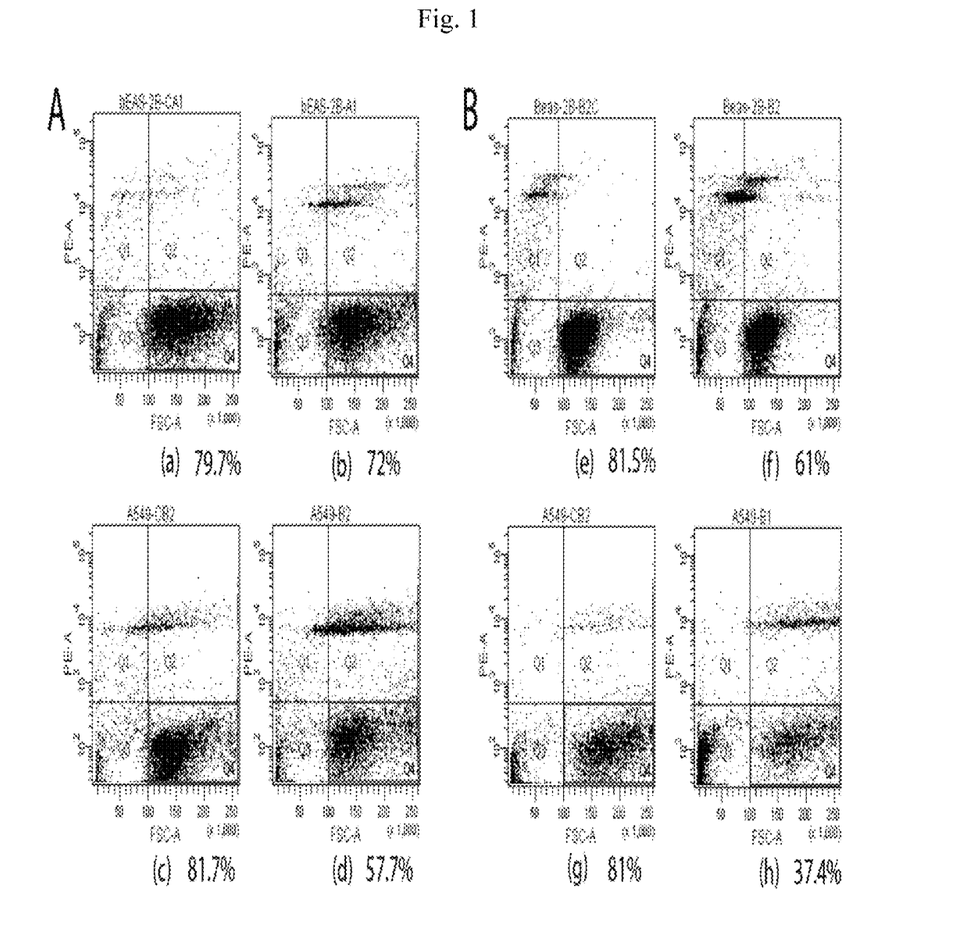
FIG. 1 shows results of flow cytometry tests of BEAS-2B and A549 cells.

The flow cytometry results of the control and ultrasound-treated cells are shown in FIG. 1. FIG. 1A shows the results with ultrasound treatment without gold nanoparticles, FIG. 1B shows the combined effect of ultrasound with gold nanoparticles. FIGS. 1a and 1c are results from untreated control samples of BEAS-2B and A549 cells, respectively. FIGS. 1b and 1d show the damaging effects of only ultrasound treatments on cells.

The number of live BEAS-2B cells decreased from 79.7% for controls to 72% with ultrasound treatment. At the same time, the number of live malignant A549 cells changed from 81.7% for control to 57.7% with the ultrasound exposure (FIGS. 1c and 1d). Thus, the overall cell damaging effect of ultrasound was more pronounced for malignant A549 cells than for healthy BEAS-2B cells.

To explore the combined effect of gold nanoparticles with ultrasound, we added gold nanoparticles with the concentration of 2.5 ppm Au/well/mL to cells before the ultrasound treatment. All other conditions of the experiment were fixed similar to the one without nanoparticles shown in FIG. 1A.

Figure 2:
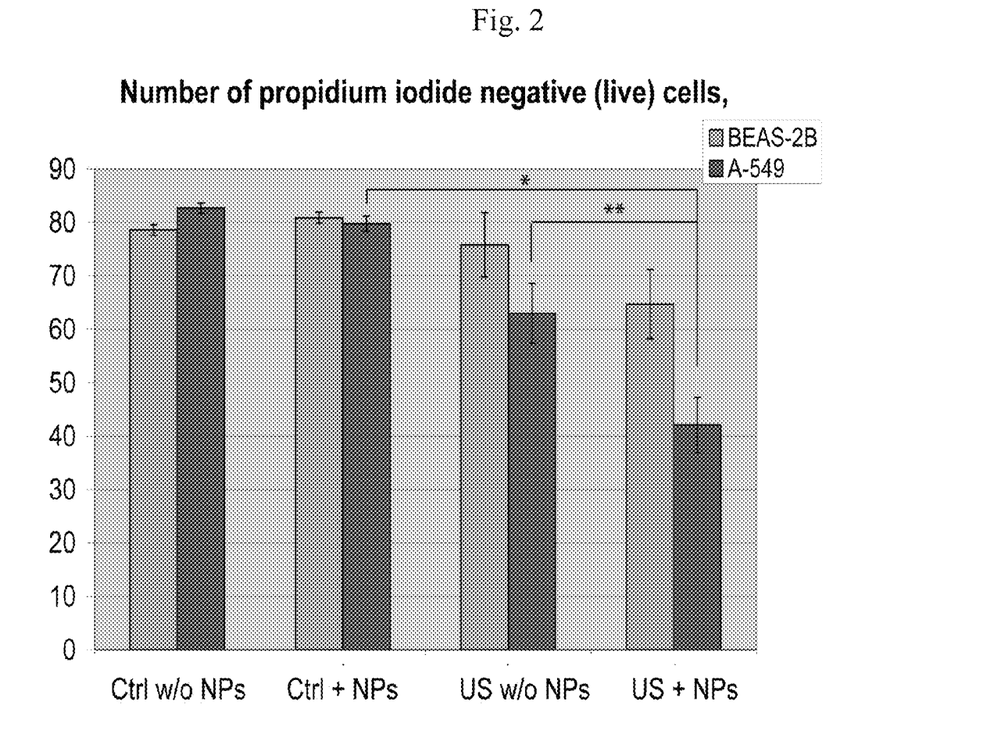
FIG. 2 shows the average percent of live BEAS-2B and A-549 cells for 5 flow cytometry experiments before and after treatment by only ultrasound as well as by NAUT. NP represents nanoparticle and US represents ultrasound.

The number of propidium iodide negative (live) BEAS-2B cells decreased from 81.5% for controls to 61% after ultrasound treatment (FIGS. 1e and 1f), while the number of live A549 cells surprisingly decreased from 81% to 37.4% (FIGS. 1g and 1h), demonstrating the higher damage of cancer cells under the combination of ultrasound with gold nanoparticles. The averaged numbers for 5 experiments of live BEAS-2B and A-549 cells are shown in FIG. 2, and recapitulated in Table 1 below. The standard deviations for the number of live cells (Q4) were calculated for three similar samples at each test and compared the variation for 5 separate tests on different days. For control samples, the standard deviation was 1 to 1.4%. For ultrasound-treated samples, the standard deviation was larger: 5 to 6.5%. T-test calculated for A-549 cells for the effect of ultrasound only was 0.1. For the combined effect of ultrasound with gold nanoparticles, the T-value was 0.003, which showed that adding nanoparticles to the system provided a surprising and statistically significant effect on necrosis of cells.

TABLE 1

Live BEAS-2B and A-549 cells after ultrasound treatment

| Cells | Control without NP | Control with NP | Ultrasound without NP | Ultrasound with NP |
|---|---|---|---|---|
| BEAS-2B | 78.6 ± 1 | 80.9 ± 1 | 75.8 ± 6 | 64.7 ± 6.5 |
| A549 | 82.7 ± 1 | 79.8 ± 1.4 | 63.0 ± 5.6 | 42.1 ± 5.2 |

Example 8

Normal and Cancerous Cells Under Identical Exposure

To compare the effect of ultrasound on normal and cancerous cells under identical ultrasound exposure, the BEAS-2B and A549 cells were co-cultured and modified with fluorescent green and red proteins, respectively. A monolayer of the co-culture was treated with ultrasound in the presence and in the absence of gold nanoparticles under the same conditions.

Figure 3:
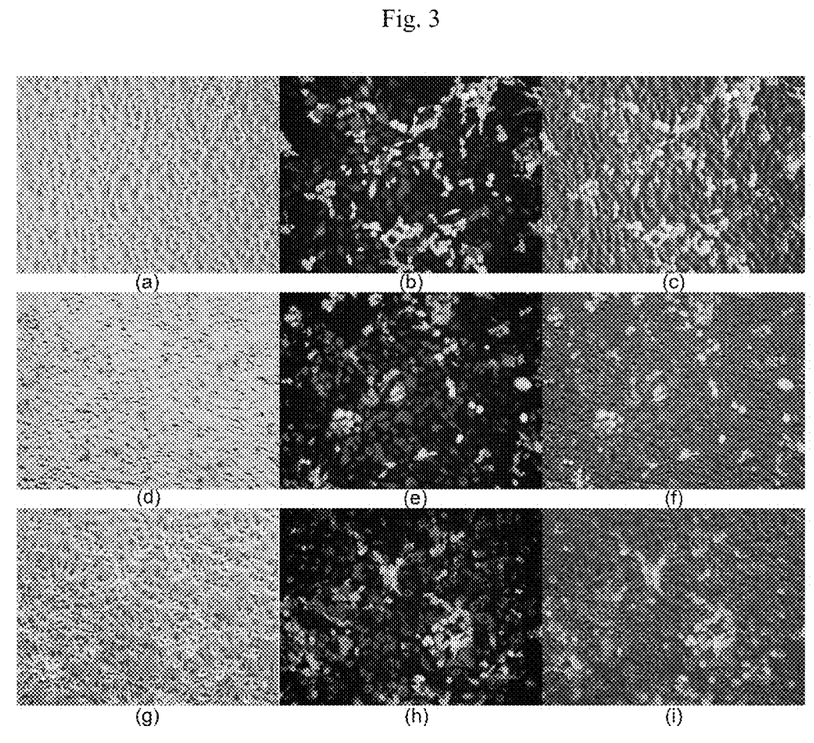
FIG. 3 shows phase contrast images of Beas-2B and A549 co-culture.

To estimate the cell damage, we analyzed the trypan blue-stained cells using optical microscopy. The phase-contrast images of the BEAS-2B/A549 co-culture treated with trypan blue are provided in FIG. 3. The images were obtained with the exposure to a mercury lamp (U-LH100HG). FIGS. 3a, 3d and 3g demonstrates the live (uncolored) and dead (blue-colored) cells. The overlaid fluorescent images of the green (BEAS-2B) and red (A549) cells produced under different colored filters are provided in FIGS. 3b, 3e and 3h. The combined fluorescent images are shown in FIGS. 3c, 3f and 3j. The number of dead cells (cells with dark-colored nuclei) was calculated and averaged for 5 random images of the co-culture in 6 similar experiments.

Images in FIG. 3a-c correspond to the control samples without gold nanoparticles: few dead cells are visible in the control samples for either cell line. Images in FIG. 3d-f show the co-cultured cells after ultrasound treatment without adding any nanoparticles—only a few dead BEAS-2B cells observed. The number of dead A549 cells was estimated at approximately 18% with a standard deviation of 5%. Images of the co-culture treated with the combination of ultrasound and gold nanoparticles are presented in FIG. 3g-i: the number of dead BEAS-2B cells was approximately 7±5%, while the number of dead A549 cells was approximately 50±15%. Thus, the experiment with the co-cultured cells indicated that the selective damage to A549 cancer cells occurred both with ultrasound only and with ultrasound in the presence of gold nanoparticles. Adding gold nanoparticles caused more damage to both cell lines, but the damage was surprisingly much greater for the cancer cells. In addition, a difference was noted in the cell damage for the co-cultured versus separate cell monolayers: the co-cultured healthy BEAS-2B cells were less sensitive to ultrasound exposure, and the selectivity of the A549 cell damage was larger. Nevertheless, the damage to the cancer cells was always surprisingly significantly greater than that to the normal cells when the NAUT was applied.

Figure 4:
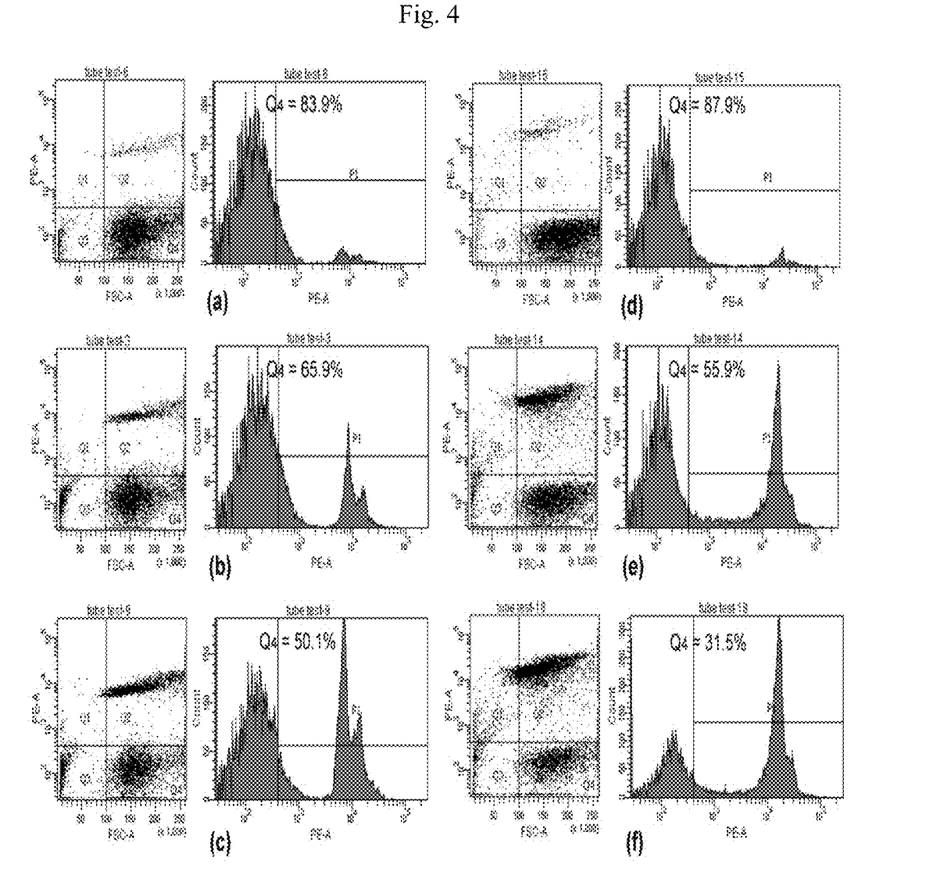
FIG. 4 shows flow cytometry images of breast healthy MCF-10A and cancer MDA-MB-231 cells. (a) Control of MCF-10A without nanoparticles; (b) MCF-10A after ultrasound treatment without nanoparticles; (c) MCF-10A after ultrasound treatment with magnetic nanoparticles; (d) Control of MDA-MB-231 without nanoparticles; (e) MDA-MB-231 after ultrasound treatment without nanoparticles; (f) MDA-MB-231 after ultrasound with magnetic nanoparticles. Q4 is the number of live cells measured by flow cytometry. Magnetic nanoparticles (MagQu, 60 nm) with the concentration of 60 ppm were used.

Similar effects were also obtained for breast malignant MDA-MB231 and non-malignant MCF-10A for combined effect of ultrasound with magnetic nanoparticles (FIG. 4).

In general, it has been found that the presence of nanoparticles increases the difference in the amount of damage done to cancerous cells over normal cells in NAUT. In our experiments, more cancer cells were killed due to ultrasound treatment than normal cells. The combined effect of ultrasound with nanoparticles increased the selectivity toward killing cancer cells over normal cells, as compared to the effect of ultrasound alone. The use of ultrasound with nanoparticles co-cultured with cells can kill a large number of cancer cells with less effect on normal cells.

Similar results were also obtained for malignant and non-malignant breast cells. The TEM images of the healthy human breast epithelial cells H-184 and the MDA-MB-231 carcinoma cells in separate monolayer cultures both before and after ultrasound treatment are provided in FIG. 5. Images (a-c) show normal breast cells, images (d-f) show cancer cells. Images (a) and (d) are controls (no ultrasound exposure); images (b) and (e) are ultrasound treated cells without adding nanoparticles. Images (c) and (f) show cells treated with combined effect of ultrasound and magnetic nanoparticles.

Figure 5:
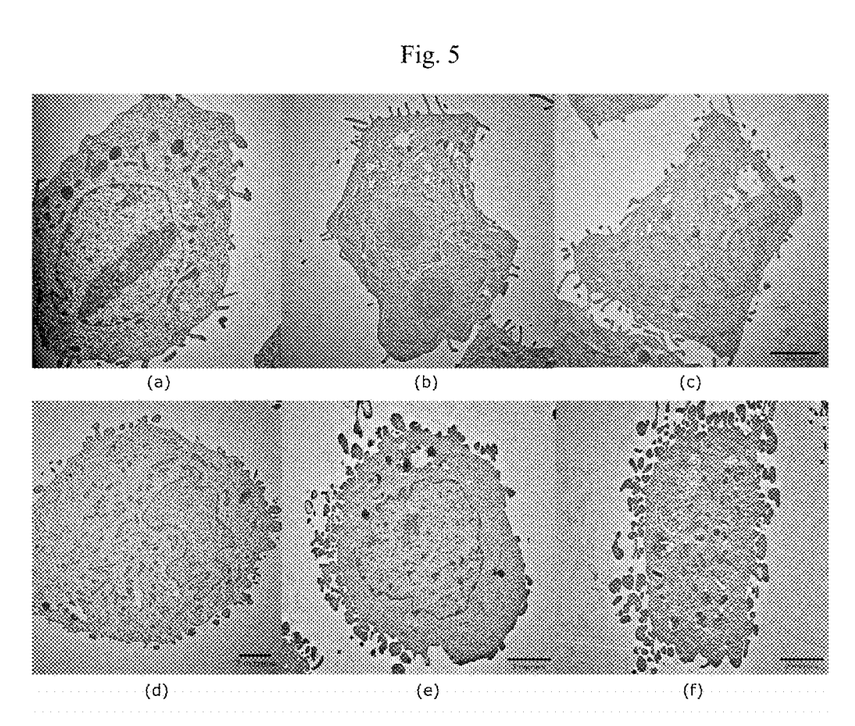
FIG. 5 shows TEM images of normal breast cells H-184B5F5/M10 (a-c) and cancer cells MDA-MB-231 cells (d-f). Images (a) and (d) are controls without ultrasound; images (b) and (e) are ultrasound-treated cells without adding nanoparticle; images (c) and (f) are cells treated with combined effect of ultrasound and magnetic nanoparticles.

As demonstrated on FIG. 5, the cell membranes of the cancer cells exhibit more damage than those of the normal cells especially for combined ultrasound effect.

The synergistic effect and selectivity of necrosis for cancer cells over normal cells by the methods of this invention allows using a low to medium intensity ultrasound for effective killing of cancer cells with decreased side effects.

Example 9

Effect of Treatment on Tumor Growth in Mice

The effects of treatments using the inventive nanoparticle-ultrasound methods of this invention were demonstrated for adenocarcinomic lung cell tumors in mice. The results showed that the nanoparticle-ultrasound methods of this invention were unexpectedly advantageous in reducing tumor size.

Human adenocarcinomic lung cells A549, number of cells $5 \times 10^6$, were subcutaneously injected into left abdominal area of 6-weeks-old male NOD/SCID mice. Mice were divided into three groups, with three mice in each group: (1) control group; (2) mice treated with only ultrasound (US); (3) mice treated with ultrasound and nanoparticle injection (US and NP). 100 uL of magnetic nanoparticles with stock concentration 1200 ug/mL were injected at intra-tumor locations three hours before ultrasound treatment. The magnetic nanoparticles had a size of 4-7 nm as measured by TEM. The magnetic nanoparticles were stabilized with polyvinylalcohol. The nanoparticles did not have a drug molecule attached.

Mice were treated with ultrasound once per week. The total number of treatments was three. Tumor volume was calculated by the formula $V=\frac{1}{2}(L \times W^2)$, where L is length and W is width of the tumor. For ultrasound treatment, Sonicator740 was used with ultrasound power at 2.2 W/cm², and duration of treatment 5 minutes, at ultrasound frequency of 3 MHz. The ultrasound transducer was placed on the tumor directly with gel as medium between the tumor and the transducer.

Results: For the control group (1) the average initial tumor size was 24.2 mm³. After the treatment days, the average tumor size for the control group (1) was 486 mm³ (20-fold increase).

For the ultrasound treated group (2), the average initial tumor size was 97.4 mm³. After the treatment days, the average size for the US group was 278 mm³ (185% increase).

For the ultrasound and nanoparticle treated group (3), the average initial tumor size was 277.6 mm³. After the treatment days, the average size for the US+NP group was 204.4 mm³ (26% decrease).

All publications and patents and literature specifically mentioned herein are incorporated by reference for all purposes. Nothing herein is to be construed as an admission that the invention is not entitled to antedate such disclosure by virtue of prior invention.

It is understood that this invention is not limited to the particular methodology, protocols, materials, and reagents described, as these may vary. It is also to be understood that the terminology used herein is for the purpose of describing particular embodiments only, and is not intended to limit the scope of the present invention which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A method for reducing the growth of adenocarcinomic lung cancer tumor cells in a subject, the method consisting of the steps:
    injecting gold nanoparticles into the subject; and
    irradiating the subject with focused ultrasound,
        wherein the spatial-peak temporal-peak intensity of the ultrasound measured in a well with 1 mL water using a calibrated needle hydrophone is less than 70 W/cm².

2. The method of claim 1, wherein the gold nanoparticles are attached to a cancer drug, a targeted cancer drug, a humanized monoclonal antibody, a chimeric monoclonal antibody, or a fully human antibody.

3. The method of claim 1, wherein the size of the nanoparticles ranges from 1 nanometer to 1000 nanometers.

4. The method of claim 1, wherein the spatial-peak temporal-peak intensity of the ultrasound measured in a well with 1 mL water using a calibrated needle hydrophone is less than 10 W/cm$^2$.

5. The method of claim 1, wherein the injecting is by parenteral injection, intravenous injection, intra-arterial injection, intramuscular injection, or subcutaneous injection.

6. The method of claim 1, wherein the nanoparticles are injected in a solution, an emulsion, or a gel.

7. The method of claim 1, wherein the gold nanoparticles are injected at a concentration of gold of 50 mg Au/cm$^3$ to 250 mg Au/cm$^3$.

8. The method of claim 1, wherein the volume of the injected nanoparticles is from 0.001 ml/g of subject weight to 0.05 ml/g of subject weight.

* * * * *